(12) United States Patent
Caparso

(10) Patent No.: US 9,604,057 B2
(45) Date of Patent: Mar. 28, 2017

(54) STIMULATION METHOD FOR A SPHENOPALATINE GANGLION, SPHENOPALATINE NERVE, VIDIAN NERVE, OR BRANCH THEREOF FOR TREATMENT OF MEDICAL CONDITIONS

(71) Applicant: Anthony V. Caparso, San Francisco, CA (US)

(72) Inventor: Anthony V. Caparso, San Francisco, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 0 days.

(21) Appl. No.: 13/746,038

(22) Filed: Jan. 21, 2013

(65) Prior Publication Data

US 2013/0190838 A1 Jul. 25, 2013

Related U.S. Application Data

(63) Continuation-in-part of application No. 13/476,224, filed on May 21, 2012, now Pat. No. 9,456,836, and
(Continued)

(51) Int. Cl.
*A61N 1/32* (2006.01)
*A61N 1/36* (2006.01)
(Continued)

(52) U.S. Cl.
CPC .......... *A61N 1/36071* (2013.01); *A61B 17/24* (2013.01); *A61B 17/3468* (2013.01); *A61N 1/0526* (2013.01); *A61N 1/3606* (2013.01); *A61B 17/3211* (2013.01); *A61B 2017/0073* (2013.01); *A61B 2017/320052* (2013.01); *A61N 1/0548* (2013.01); *A61N 1/0551* (2013.01); *A61N 1/36017* (2013.01); *A61N 1/36021* (2013.01);
(Continued)

(58) Field of Classification Search
CPC .......... A61N 1/36021; A61N 1/360526; A61N 1/3606; A61N 1/36071; A61N 1/36075; A61N 1/36082; A61N 1/0529; A61N 1/0531; A61N 1/36025; A61N 1/0526; A61N 1/0551; A61B 17/24; A61B 17/3468
USPC .......................... 607/2, 45–46, 53, 115–118
See application file for complete search history.

(56) References Cited

U.S. PATENT DOCUMENTS 6,405,079 B1 * 6/2002 Ansarinia .................. 607/2
2003/0018368 A1 * 1/2003 Ansarinia ............ A61N 1/3605
607/46

(Continued)

*Primary Examiner* — Christopher D Koharski
*Assistant Examiner* — Pamela M Bays
(74) *Attorney, Agent, or Firm* — Tarolli, Sundheim, Covell & Tummino LLP

(57) ABSTRACT

One aspect of the present disclosure relates to a method for suppressing or preventing a medical condition in a subject. One step of the method can include positioning at least one electrode on or proximate to at least one of a sphenopalatine ganglion (SPG), a sphenopalatine nerve (SPN), a vidian nerve (VN), or a branch thereof, of the subject. Next, the at least one electrode can be activated to apply an electrical signal to at least one of the SPG, the SPN the VN, or the branch thereof. The medical condition can include pain resulting from one or more of atypical odontalgia, cluster tic syndrome, geniculate neuralgia, occipital neuralgia and temporal arteritis.

11 Claims, 2 Drawing Sheets

Related U.S. Application Data a continuation-in-part of application No. 13/470,480, filed on May 14, 2012, now Pat. No. 9,220,524.

(60) Provisional application No. 61/588,813, filed on Jan. 20, 2012.

(51) Int. Cl.

| | | |
|---|---|---|
| *A61B 17/24* | (2006.01) | |
| *A61B 17/34* | (2006.01) | |
| *A61N 1/05* | (2006.01) | |
| *A61N 1/375* | (2006.01) | |
| *A61B 17/3211* | (2006.01) | |
| *A61B 17/32* | (2006.01) | |
| *A61B 17/00* | (2006.01) | |

(52) U.S. Cl.
CPC ...... *A61N 1/36153* (2013.01); *A61N 1/36157* (2013.01); *A61N 1/36171* (2013.01); *A61N 1/36175* (2013.01); *A61N 1/375* (2013.01)

(56) References Cited

U.S. PATENT DOCUMENTS

| | | | |
|---|---|---|---|
| 2003/0176898 A1* | 9/2003 | Gross et al. | 607/54 |
| 2005/0065574 A1* | 3/2005 | Rezai | 607/45 |
| 2005/0159790 A1* | 7/2005 | Shalev | 607/45 |
| 2005/0283197 A1* | 12/2005 | Daum | A61N 1/36521 607/17 |
| 2006/0095088 A1* | 5/2006 | De Ridder | A61N 1/3605 607/48 |
| 2006/0206155 A1* | 9/2006 | Ben-David | A61N 1/0556 607/9 |
| 2008/0300655 A1* | 12/2008 | Cholette | A61N 1/0556 607/60 |
| 2009/0012577 A1* | 1/2009 | Rezai | A61N 1/0551 607/46 |
| 2009/0024176 A1* | 1/2009 | Yun | A61N 1/3627 607/20 |
| 2010/0185258 A1* | 7/2010 | Papay | 607/45 |
| 2011/0137381 A1* | 6/2011 | Lee et al. | 607/62 |

\* cited by examiner

STIMULATION METHOD FOR A SPHENOPALATINE GANGLION, SPHENOPALATINE NERVE, VIDIAN NERVE, OR BRANCH THEREOF FOR TREATMENT OF MEDICAL CONDITIONS

RELATED APPLICATIONS

The present application is a continuation-in-part of U.S. patent application Ser. No. 13/476,224, filed May 21, 2012, and Ser. No. 13/470,480, filed May 14, 2012, and also claims the benefit of U.S. Provisional Patent Application Ser. No. 61/588,813, filed Jan. 20, 2012. Each of the aforementioned applications is hereby incorporated by reference in its entirety.

TECHNICAL FIELD

The present disclosure relates generally to neuromodulatory methods, and more particularly to methods for treating medical conditions by stimulation of a sphenopalatine ganglion, a sphenopalatine nerve, a vidian nerve, or a branch thereof.

BACKGROUND

Neuralgias, such as trigeminal, sphenopalatine, and occipital neuralgias may start at any age, although trigeminal neuralgia is more common among the elderly. From a pathophysiological standpoint, pain arising due to neuralgias always originates from, and is transmitted by, the involved nerve. Accordingly, neuralgias may be caused by direct injury to nerves in the form of trauma, infection (e.g., herpes), neuroma formation or demyelination. Pain arising due to neuralgia may be brief and paroxysmal or continuous, and numerous attacks may occur throughout the day. Neuralgias do not feature seasonal or diurnal patterns in the onset of pain. Trigeminal neuralgia often has an associated "trigger zone" on the face, which can trigger the onset of the pain. Sphenopalatine neuralgia often has autonomic features, which are not commonly found in other neuralgias. In occipital neuralgia, the occipital nerve is usually tender to palpation and pain can be manifested anywhere along the course of the nerve.

Historically, neuralgias have been treated using medication, invasive procedures and, rarely, electrical stimulation of cranial nerves. Newer techniques have been developed for treating a variety of neurological disorders including electrical stimulation of cranial nerves, such as the glossopharangeal, vagus or trigeminal nerves. U.S. Pat. No. 5,540,734 to Zabara, for example, describes a suggested therapeutic modality for a variety of medical, psychiatric, and neurological disorders in which modulating electrical signals are applied to either or both of the trigeminal and glossopharyngeal nerves using electrodes. The principle behind these approaches is to disrupt or modulate abnormal neuronal transmissions in the nervous system through the application of electrical signals.

The use of medications to treat the above-described conditions can result in systemic side-effects of wide-ranging severity. Invasive techniques used to destroy tissues, such as lesioning, resecting, freezing or burning, are typically non-reversible, and the treatment cannot be adjusted once applied. Destruction of the tissue may itself lead to significant side effects, such as deafferentation pain.

SUMMARY

The present disclosure relates generally to neuromodulatory methods, and more particularly to methods for treating medical conditions by stimulation of a sphenopalatine ganglia (SPG), a sphenopalatine nerve (SPN), a vidian nerve (VN), or a branch thereof.

One aspect of the present disclosure relates to a method for suppressing or preventing a medical condition in a subject. One step of the method can include positioning at least one electrode on or proximate to at least one of a SPG, a SPN, a VN, or a branch thereof, of the subject. Next, the at least one electrode can be activated to apply an electrical signal to at least one of the SPG, the SN, the VN, or the branch thereof. The medical condition can include pain resulting from one or more of atypical odontalgia, cluster tic syndrome, geniculate neuralgia, occipital neuralgia and temporal arteritis.

Another aspect of the present disclosure relates to a method for suppressing or preventing a medical condition in a subject. One step of the method can include positioning at least one electrode on or proximate to at least one of a SPG, a SPN, a VN, or a branch thereof, of the subject. Next, the at least one electrode can be activated to apply an electrical signal to at least one of the SPG, the SPN, the VN, or the branch thereof. The medical condition can include autonomic dysfunction resulting from one or more of Holmes-Adie syndrome, orthostatic hypotension, striatonigral degeneration, vasovagal syncope, Lyme disease and autonomic instability.

Another aspect of the present disclosure relates to a method for suppressing or preventing a medical condition in a subject. One step of the method can include positioning at least one electrode on or proximate to at least one of a SPG, a SPN, a VN, or a branch thereof, of the subject. Next, the at least one electrode can be activated to apply an electrical signal to at least one of the SPG, the SPN, the VN, or the branch thereof. The medical condition can include a neurological disorder resulting from one or more of hemifacial spasm, Melkersson-Rosenthal syndrome and Parry-Romberg syndrome.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
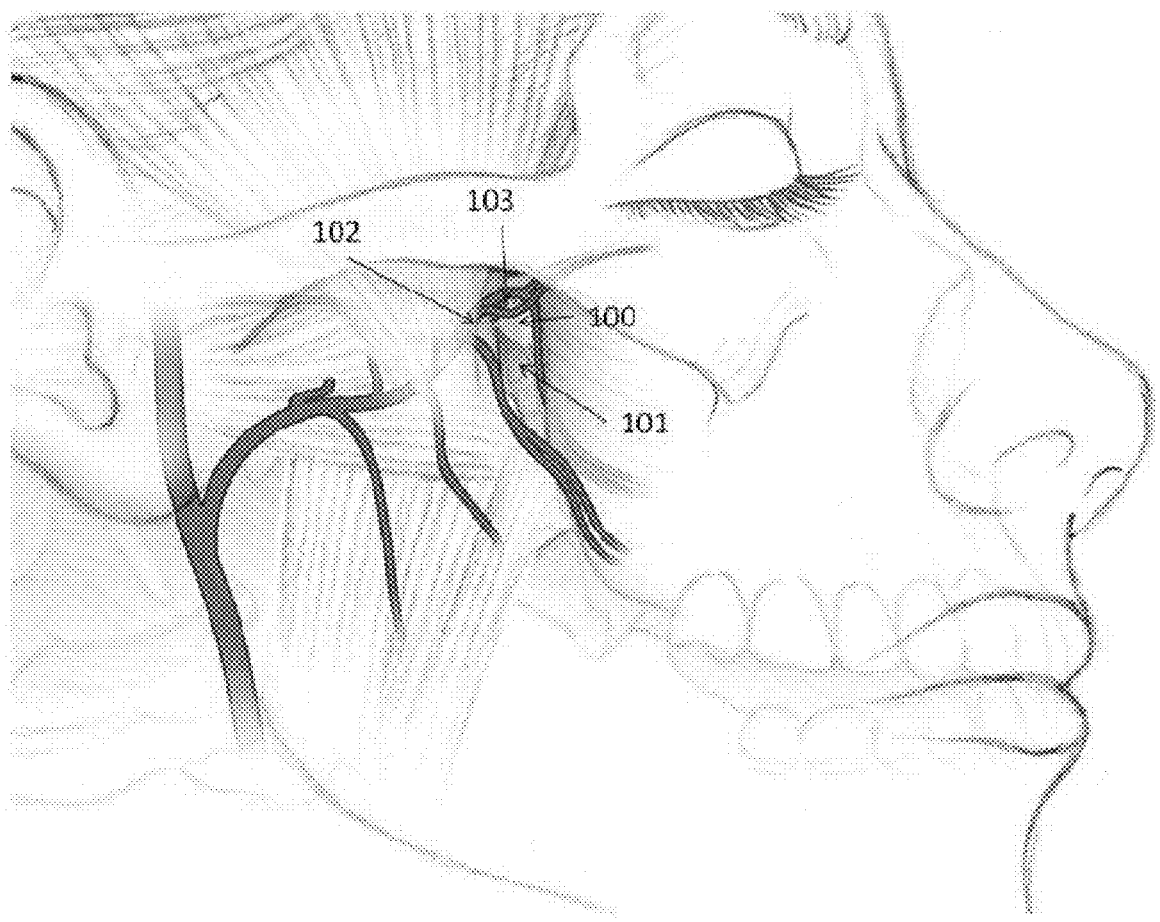
FIG. 1 is a schematic illustration of a lateral view of a human skull showing the position of the infratemporal fossa with the sphenopalatine ganglion (SPG) lying within the sphenopalatine fossa, surrounded by the anterior margin of the lateral pterygoid plate and the posterior wall of the maxillary sinus.

Unless defined otherwise, all technical and scientific terms used herein have the same meaning as is commonly understood by one of skill in the art to which the present disclosure pertains.

In the context of the present disclosure, the term "in communication" can refer to at least a portion of an electrode being adjacent, in the general vicinity, in close proximity, or directly next to and/or directly on a target nerve or nerve structure, such as a sphenopalatine ganglion (SPG), a sphenopalatine nerve (SPN) (also called the "pterygopalatine nerve"), a vidian nerve (VN) (also called "the nerve of the pterygoid canal"), or a branch thereof (e.g., a nasopalatine nerve, a greater palatine nerve, a lesser palatine nerve, a superior maxillary nerve, a greater petrosal nerve, or a lesser petrosal nerve). In some instances, the term can mean that at least a portion of an electrode is "in communication" with a target nerve or nerve structure if application of a therapy signal (e.g., an electrical signal) thereto results in a modulation of neuronal activity to elicit a desired response, such as modulation of a sensory signal generated in, or transmitted through, the target nerve or nerve structure.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the terms "modulate" or "modulating" with reference to activity of a target nerve or nerve structure can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the terms "substantially blocked" or "substantially block" when used with reference to activity of a target nerve or nerve structure can refer to a complete (e.g., 100%) or partial inhibition (e.g., less than 100%, such as about 90%, about 80%, about 70%, about 60%, or less than about 50%) of nerve conduction therethrough. For example, the terms "block", "blocking", and "blockade" can refer to the disruption, modulation, and/or inhibition of nerve impulse transmissions through a target nerve or nerve structure.

As used herein, the term "activity" when used with reference to a target nerve or nerve structure can, in some instances, refer to the ability of a nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on a nerve, neuron, or fiber of a target nerve or nerve structure.

As used herein, the terms "prevent" or "preventing" when used with reference to a medical condition can refer to stopping a medical condition from occurring, or taking advance measures against the possibility or probability that a medical condition will happen or occur. In some instances, the terms can refer to an action or actions taken to decrease the chance that a subject will contract, develop, or suffer from a medical condition.

As used herein, the terms "suppress" or "suppressing" when used with reference to a medical condition can refer to refer to any quantitatively or qualitatively measurable or observable reduction or attenuation in a medical condition (e.g., a sign or symptom associated with the medical condition).

As used herein, the term "medical condition" can refer to any condition, state, or disease that is characterized, at least in part, by a disruption in sensory signals passing through or associated with the autonomic nervous system (ANS). Non-limiting examples of medical conditions can include pain, autonomic disorders, and neurological disorders.

As used herein, the terms "treat" or "treating" can refer to therapeutically regulating, preventing, improving, alleviating the symptoms of, and/or reducing the effects of a medical condition. As such, treatment also includes situations where a medical condition, or at least symptoms associated therewith, is completely inhibited, e.g., prevented from happening or stopped (e.g., terminated) such that the subject no longer suffers from the medical condition, or at least the symptom(s) that characterize the medical condition.

Overview

A brief discussion of the pertinent neurophysiology is provided to assist the reader with understanding certain aspects of the present disclosure.

The sphenopalatine ganglion (SPG) 100 (FIG. 1), also called the pterygopalatine ganglion, is located within the pterygopalatine fossa (PPF) 101. The PPF 101 is bounded anteriorly by the maxilla, posteriorly by the medial plate of the pterygoid process and greater wing of the sphenoid process, medially by the palatine bone, and superiorly by the body of the sphenoid process. Its lateral border is the pterygomaxillary fissure, which opens to the infratemporal fossa.

The SPG 100 is a large, extra-cranial parasympathetic ganglion. The SPG 100 is a complex neural ganglion with multiple connections, including autonomic, sensory and motor. The maxillary branch of the trigeminal nerve and the nerve of the pterygoid canal, also known as the vidian nerve (VN) 102 sends neural projections to the SPG 100. The fine branches from the maxillary nerve—known as the pterygopalatine nerves or sphenopalatine nerves (SPN) 103—form the sensory component of the SPG 100. The SPN 103 pass through the SPG 100 and do not synapse. The greater petrosal nerve carries the preganglionic parasympathetic axons from the superior salivary nucleus to the SPG 100. These fibers synapse onto the postganglionic neurons within the SPG 100. The deep petrosal nerve connects the superior cervical sympathetic ganglion to the SPG 100, and carries postganglionic sympathetic axons that again pass through the SPG without any synapses.

The deep and greater petrosal nerves join together just before entering the pterygoid canal to form the VN 102. The VN 102 is housed within the Vidian canal, which is posterior to the SPG 100. The VN 102 connects to the SPG 100 and contains parasympathetic fibers which synapse in the SPG, sensory fibers which provide sensation to part of the nasal septum, and also sympathetic fibers. The SPN 103 are sensory nerves that connect the SPG 100 to the maxillary nerve. The SPN 103 traverse through the SPG 100 without synapsing and proceed to provide sensation to the palate. The SPN 103 suspend the SPG 100 in the PPF 101.

The present disclosure relates generally to neuromodulatory methods, and more particularly to methods for treating medical conditions by stimulation of a SPG 100, SPN 103, VN 102, and/or a branch thereof, such as a nasopalatine nerve, a greater palatine nerve, a lesser palatine nerve, a superior maxillary nerve, a greater petrosal nerve, or a lesser petrosal nerve. As discussed in more detail below, the present disclosure provides methods for suppressing or preventing medical conditions by disrupting sensory signals passing through the ANS, such as pain signals. The abnormal regulation of pain or autonomic pathways, which may be a feature of the medical conditions disclosed herein, can cause excitation, loss of inhibition, suppression, or loss of excitation of these pathways. Thus, in some instances, the present disclosure provides methods for applying one or more therapy signals to a target nerve or nerve structure (e.g., a SPG 100, SPN 103, VN 102 and/or a branch thereof) to modulate the transmission of sensory signals and stimulate or block the autonomic pathways passing through the target nerve or nerve structure to reduce or eliminate one or more symptoms or signs associated with the medical condition. Similarly, application of one or more therapy signals to a target nerve or nerve structure (e.g., a SPG 100, SPN 103, VN 102 and/or a branch thereof) can modulate the transmission of sensory signals other than pain responsible for provoking or aggravating other undesirable sensations or conditions, such as nausea, bladder disorders, sleep disorders or abnormal metabolic states.

Methods

One aspect of the present disclosure can include a method for suppressing, preventing, or treating a medical condition in a subject. Methods of the present disclosure can generally include the steps of: positioning at least one electrode on or proximate to a target nerve or nerve structure (e.g., a SPG 100, SPN 103, VN 102 and/or a branch thereof) of the subject; and activating the at least one electrode to apply a therapy signal (e.g., an electrical signal) to the target nerve or nerve structure. In some instances, the methods of the present disclosure can act to suppress or prevent a medical condition by disrupting sensory signals passing through the ANS as the signals traverse or are generated in the target nerve or nerve structure.

In some instances, medical conditions that can be suppressed, prevented, or treated by the present disclosure can include pain resulting from one or more of atypical odontalgia, cluster tic syndrome, geniculate neuralgia, occipital neuralgia, and temporal arteritis. Without wishing to be bound by theory, it is believed that the abnormal regulation of pain pathways can cause excitation or a loss of inhibition of those pathways, resulting in an increased perception of pain. Thus, applying one or more therapy signals (e.g., an electrical signal) to a target nerve or nerve structure (e.g., a SPG 100, SPN 103, VN 102 and/or a branch thereof) can substantially block the transmission of pain signals and stimulate inhibitory feedback of the pain pathways passing therethrough to reduce or eliminate pain experienced by the subject.

In other instances, medical conditions that can be suppressed, prevented, or treated by the present disclosure can include autonomic dysfunction resulting from one or more of Holmes-Adie syndrome, orthostatic hypotension, striatonigral degeneration, vasovagal syncope, Lyme disease and autonomic instability.

In further instances, medical conditions that can be suppressed, prevented, or treated by the present disclosure can include a neurological disorder resulting from one or more of hemifacial spasm, Melkersson-Rosenthal syndrome and Parry-Romberg syndrome.

In another aspect, the at least one electrode can include any mono-polar, bipolar, or multi-polar electrode configured to deliver an electrical signal to a target nerve or nerve structure (e.g., a SPG 100, SPN 103, VN 102 and/or a branch thereof). In some instance, the at least one electrode can be securely disposed on or within a housing or casing (e.g., made of silicon, metal or plastic). In other instances, the at least one electrode can be securely disposed on a percutaneous lead. In further instances, the at least one electrode can comprise one component of a neurostimulator. In such instances, the neurostimulator can comprise any active implantable medical device configured to deliver electrical stimulation, alone or in combination with other types of stimulation, to a target nerve or nerve structure (e.g., a SPG 100, SPN 103, VN 102 and/or a branch thereof) of a subject. The neurostimulator can further include any active implantable medical device configured for implantation for a relatively short period of time (e.g., to address acute medical conditions) or a relatively long period of time (e.g., to address chronic medical conditions). Additionally, the neurostimulator can include one or more elements used to record or monitor a physiological response of a subject's tissue (e.g., a delivered therapy), as well as one or more other components that interface with the subject's tissue (e.g., therapeutic agent delivery mechanisms, sensors, etc.). The neurostimulator can further include, or at least be in electrical communication with, a power source that provides the energy source for electrical stimulation.

One or a combination of surgical methods may be used to implant the at least one electrode on or adjacent a target nerve or nerve structure (e.g., a SPG 100, SPN 103, VN 102 and/or a branch thereof) such that the at least one electrode is in electrical communication with the target nerve or nerve structure. In some instances, a percutaneous technique can be used to implant the at least one electrode. Examples of percutaneous techniques that may be employed are disclosed in U.S. Pat. No. 6,526,318 (hereinafter, "the '318 patent"), as well as U.S. patent application Ser. No. 13/476,224 (hereinafter, "the "224 application") and Ser. No. 13/470,480 (hereinafter, "the '480 application"). Because the SPG 100, VN 102, and SPN 103 are in very close proximity to one another within a very small area, the same technique can be applied to achieve placement of at least one electrode on or adjacent to any of the three structures. It should also be understood that, because the region in which the SPG 100, VN 102, and SPN 103 all join together is very small, stimulation of the SPG, VN, or SPN (or a branch thereof), even when an electrode is placed optimally, may also stimulate two or all of the other structures. It will also be understood that at least one electrode can be positioned on the skin of a subject adjacent a target nerve or nerve structure (e.g., a SPG 100, SPN 103, VN 102 and/or a branch thereof) so that an electrical signal can be transcutaneously delivered to the target nerve or nerve structure.

In some instances, the at least one electrode can be implanted in the subject without penetrating the cranium of the subject.

In other instance, the at least one electrode can be implanted in the subject without penetrating the nasal cavity or the palate of the subject.

In another aspect, a therapy signal can be applied to the target nerve or nerve structure (e.g., a SPG 100, SPN 103, VN 102 and/or a branch thereof) to modulate activity associated with the target nerve or nerve structure and thereby prevent or suppress the medical condition. Neuromodulation of the SPG 100, for example, can be done directly or indirectly by affecting postganglionic neurons located within the SPG and/or their corresponding axons, or the preganglionic axons in the VN 102 that synapse with the SPG, respectively. Examples of therapy signals that may be applied to a target nerve or nerve structure can include electrical energy, chemical agents, mechanical force, thermal energy, and combinations thereof.

In some instances, the therapy signal can be an electrical signal. Electrical stimulation may be delivered in any of several forms, such as biphasic charge-balanced pulses having a frequency of about 1-1000 Hz (e.g., 5-200 Hz), a pulse-width of about 0.04-2 ms, a current of about 0.05-100 mA (e.g., 0.1-5 mA), and a voltage of about 1-10 V. In addition, electrical modulation can be controllable such that either anodic or cathodic stimulation may be applied. Stimulation may be delivered continuously, intermittently, as a burst in response to a control signal, or as a burst in response to a sensed parameters, such as increased SPG neural activity. The electrical parameters may also be adjusted automatically based on a control signal, based on sensed parameters, or by selection by the subject.

In some instances, electrical energy can be applied to a target nerve or nerve structure (e.g., a SPG 100, SPN 103, VN 102 and/or a branch thereof) for a time and in an amount insufficient to cause a lesion on the target nerve or nerve structure.

In another aspect, an electrode may be utilized which, instead of or in addition to delivering electrical stimulation to the target nerve or nerve structure, delivers a medication solution or analgesic to the target nerve or nerve structure. For example, an electrode may be used that has a small port at its tip, which is connected to a reservoir or medication pump containing a medication solution or an analgesic (e.g., an anesthetic solution). The medication/analgesic delivery electrode may be implanted using the same procedure as used for the electrical stimulation electrode. If desired by the subject or physician, the reservoir or medication pump may also be implanted in the subject's body (e.g., similar or identical to an implantable pulse generator). In some instances, the electrode can be controllable such that the amount of medication solution or analgesic applied, the rate at which medication solution or analgesic is applied, and the time period over which the medication solution or analgesic is applied is adjustable.

It should be understood that delivery of a medication solution or analgesic from an electrode may be used alone or in conjunction with the electrical stimulation method described above. For example, an electrode may be used that is capable of either producing an electrical signal or delivering a medication solution or analgesic. As another example, an electrostimulatory approach could be applied to a target nerve or nerve structure (e.g., a SPG 100, SPN 103, VN 102 and/or a branch thereof) of one side of a subject's face, while the method utilizing delivery of a medication solution or analgesic could be applied to the SPG, SPN, VN, 102 and/or a branch thereof on the other side of the subject's face.

Advantageously, once the at least one electrode is placed into communication with the target nerve or nerve structure, application of one or more therapy signals (e.g., electrical signals) can be adjusted to the subject's individual needs (e.g., by the subject or via a closed-loop system) without requiring further surgical intervention.

In one example of the present disclosure, a neurostimulator 200 (FIG. 2) can be implanted in or about the PPF 101 to deliver an electrical signal to a SPG 100, SPN 103 and/or VN 102. The neurostimulator 200 can be configured identically or similarly as the neurostimulator 200 disclosed in the '224 application. For instance, the neurostimulator 200 can include a pulse generator 201, an integral lead system 202, and an integral fixation plate 203. The neurostimulator 200 can be delivered to the PPF 101 in an identical or similar fashion as disclosed in the '480 application. Briefly, for example, a gingival-buccal surgical approach can be used whereby a trans-oral incision is first created. An introducer (not shown) is then inserted into the incision and advanced posteriorly, superiorly and medially toward the PPF 101. The introducer is carefully advanced so as to maintain contact with the posterior maxilla.

Figure 2:
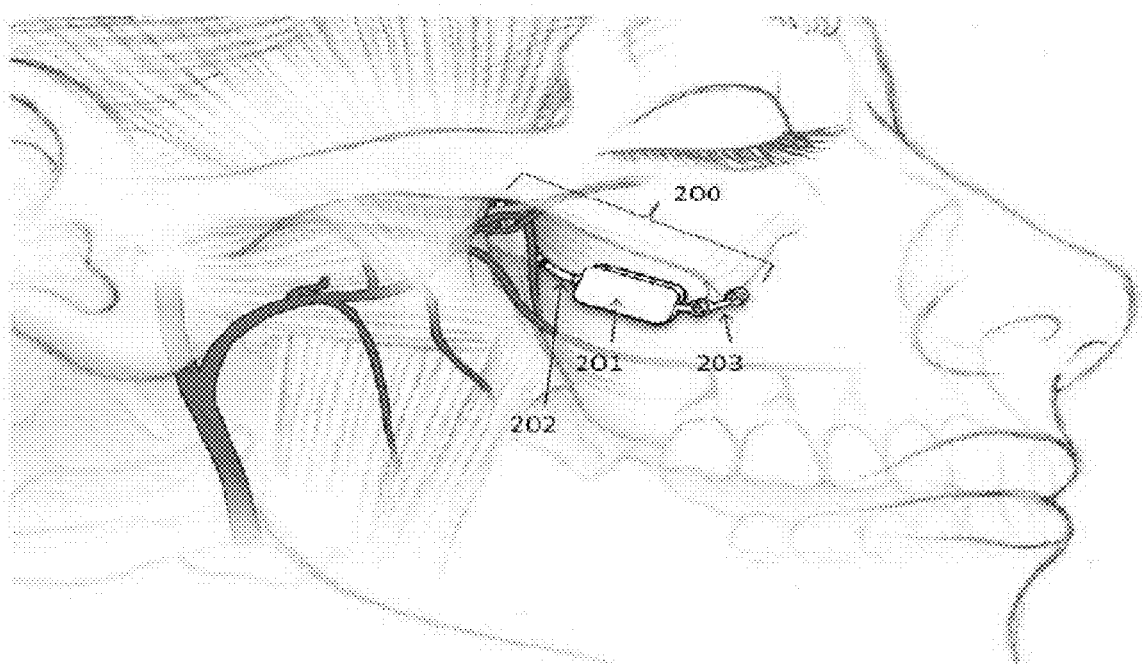
FIG. 2 is a schematic illustration showing a neurostimulator implanted on the human skull in FIG. 1 according to one aspect of the present disclosure.

Once a distal end of the introducer is placed within the PPF 101, the neurostimulator 200 can be advanced within a predefined groove of the introducer into the PPF. The neurostimulator 200 is surgically placed such that the integral lead 202 (with at least one stimulation electrode (not shown)) located within the PPF 101 directly on or adjacent to the SPG 100, SPN 103, VN 102 and/or a branch thereof. As shown in FIG. 2, the integral fixation plate 203 of the neurostimulator 200 is securely anchored to the zygomatic process of the maxilla. Following fixation of the neurostimulator 200, the neurostimulator can be activated so that the stimulation electrode delivers an electrical signal to the SPG 100, SPN 103, VN 102 and/or a branch thereof to modulate (e.g., substantially block) sensory signal transmission therethrough.

From the above description of the present disclosure, those skilled in the art will perceive improvements, changes and modifications. For example, it will be appreciated that the methods of the present disclosure can be performed to apply modulate activity of a target nerve or nerve structure (e.g., a SPG 100, SPN 103, VN 102 and/or a branch thereof) on either or both sides of a subject's head. Such improvements, changes, and modifications are within the skill of those in the art and are intended to be covered by the appended claims. All patents, patent applications, and publication cited herein are incorporated by reference in their entirety.

The following is claimed:

1. A method for suppressing or preventing autonomic dysfunction, the method comprising the steps of:
   receiving at least one electrode on or proximate to at least one of a sphenopalatine ganglion, a sphenopalatine nerve, a vidian nerve, or a branch thereof, of a subject suffering from one or more of Holmes-Adie syndrome, orthostatic hypotension, striatonigral degeneration, vasovagal syncope, and Lyme disease; and
   activating the at least one electrode, wherein the electrode is configured to apply an electrical signal to at least one of the sphenopalatine ganglion, the sphenopalatine nerve, the vidian nerve, or the branch thereof;
   wherein the at least one electrode is received without penetrating the palate and without entering into the nasal cavity; and
   suppressing or preventing the autonomic dysfunction in the subject.

2. The method of claim 1, wherein the at least one electrode is received without penetrating the cranium, into the pterygopalatine fossa so that the at least one electrode is received on or proximate to at least one of the sphenopalatine ganglion, the sphenopalatine nerve, the vidian nerve, or the branch thereof.

3. The method of claim 1, wherein the activating step generates heat insufficient to cause a lesion on at least one of the sphenopalatine ganglia, the sphenopalatine nerve, the vidian nerve, or the branch thereof.

4. The method of claim 1, wherein the activating step is performed by the subject.

5. The method of claim 1, further including the step of adjusting the electrical signal without requiring an invasive procedure on the subject.

6. A method for suppressing or preventing a neurological disorder, the method comprising the steps of:

receiving at least one electrode on or proximate to at least one of a sphenopalatine ganglion, a sphenopalatine nerve, a vidian nerve, or a branch thereof, of a subject suffering from one or more of Melkersson-Rosenthal syndrome and Parry-Romberg syndrome; and activating the at least one electrode, wherein the electrode is configured to apply an electrical signal to at least one of the sphenopalatine ganglion, the sphenopalatine nerve, the vidian nerve, or the branch thereof;

wherein the at least one electrode is received without penetrating the palate and without entering into the nasal cavity; and suppressing or preventing the neurological disorder in the subject.

7. The method of claim 6, wherein the electrical signal disrupts pain signal generation in, or transmission through, at least one of the sphenopalatine ganglion, the sphenopalatine nerve, the vidian nerve, or the branch thereof.

8. The method of claim 6, wherein the at least one electrode is received without penetrating the cranium, into the pterygopalatine fossa so that the at least one electrode is received on or proximate to at least one of the sphenopalatine ganglion, the sphenopalatine nerve, the vidian nerve, or the branch thereof.

9. The method of claim 6, wherein the activating step generates heat insufficient to cause a lesion on at least one of the sphenopalatine ganglion, the sphenopalatine nerve, the vidian nerve, or the branch thereof.

10. The method of claim 6, wherein the activating step is performed by the subject.

11. The method of claim 6, further including the step of adjusting the electrical signal without requiring an invasive procedure on the subject.

* * * * *